(12) United States Patent
Cindric et al.

(10) Patent No.: US 8,647,880 B2
(45) Date of Patent: Feb. 11, 2014

(54) MASS SPECTROMETRY-BASED PROTEIN IDENTIFICATION METHOD WITH SELECTIVE N-TERMINUS DERIVATIZATION

(75) Inventors: Mario Cindric, Zagreb (HR); Sandra Kraljevic Pavelic, Zagreb (HR); Anita Horvatic, Zagreb (HR); Ivana Dodig, Zagreb (HR)

(73) Assignee: Rudjer Bosckovic Institute (HR)

( * ) Notice: Subject to any disclaimer, the term of this patent is extended or adjusted under 35 U.S.C. 154(b) by 0 days.

(21) Appl. No.: 13/093,576

(22) Filed: Apr. 25, 2011

(65) Prior Publication Data

US 2011/0212531 A1  Sep. 1, 2011

Related U.S. Application Data

(63) Continuation of application No. PCT/HR2011/000002, filed on Jan. 11, 2011.

(30) Foreign Application Priority Data

Jan. 25, 2010 (HR) ............................. P 20100044 A

(51) Int. Cl.
  *G01N 27/00* (2006.01)
  *G01N 1/28* (2006.01)
  *G01N 33/58* (2006.01)
  *G01N 33/68* (2006.01)

(52) U.S. Cl.
  USPC ............................. 436/89; 436/173; 436/174

(58) Field of Classification Search
  None
  See application file for complete search history.

(56) References Cited

U.S. PATENT DOCUMENTS 7,338,806 B2 *  3/2008  Chen et al. .................... 436/57

FOREIGN PATENT DOCUMENTS

| EP | 1561755 A2 | 8/2005 |
|---|---|---|
| WO | 0043792 A2 | 7/2000 |
| WO | 0208767 A2 | 1/2002 |
| WO | 02095412 A2 | 11/2002 |
| WO | 02095419 A2 | 11/2002 |
| WO | 2005078451 A1 | 8/2005 |

OTHER PUBLICATIONS

Hassell, K. M. et al. "Gas-Phase Bioconjugation of Peptides via Ion/Ion Charge Inversion: Schiff Base Formation on the Conversion of Cations to Anions," Anal. Chem. 2010, 82, 1594-1597; published online Feb. 1, 2010.*

Han, H. et al. "Selective Covalent Bond Formation in Polypeptide Ions via Gas-Phase Ion/Ion Reaction Chemistry," J. Am. Chem. Soc. 2009, 131, 12884-12885.*

Griffiths, W. J. et al. "Negative-ion Electrospray Mass Spectra of Peptides Derivatized with 4-Aminonaphthalenesulphonic Acid," Rapid Communications in Mass Spectrometry 1995, 9, 667-676.*

Nabetani, T. et al. "Analysis of acidic peptides with a matrix-assisted laser desorption/ionization mass spectrometry using positive and negative ion modes with additive monoammonium phosphate," Proteomics 2006, 6, 4456-4465.*

(Continued)

*Primary Examiner* — Yelena G Gakh
*Assistant Examiner* — Michelle Adams
(74) *Attorney, Agent, or Firm* — St. Onge Steward Johnston & Reene LLC

(57) ABSTRACT

A method of detection of amino acid sequences and/or identification of proteins and peptides is based on derivatization of peptides or proteins using compounds comprising two or more sulfonyl groups, and subsequent analysis of the derivatized analytes using a mass spectrometer in its negative mode of operation.

6 Claims, 4 Drawing Sheets

(56) References Cited

OTHER PUBLICATIONS

Roberts, M. J. et al. "Chemistry for peptide and protein PEGylation," Advanced Drug Delivery Reviews 54 (2002) 459-476.*

Basie E. et al. "Protein Chemical Modification on Endogenous Amino Acids," Chemistry & Biology, vol. 17, Issue 3, 2010, 213-227.*

Jentoft, N. et al. "Labeling of Proteins by Reductive Methylation Using Sodium Cyanoborohydride," J. Biol. Chem. 1979, 254:4359-4365.*

Keough, et al.; "A Method for High-Sensitivity Peptide Sequencing Using Postsource Decay Matrix-Assisted Laser Desorption Ionization Mass Spectrometry", Proc. Natl. Acad. Sci. USA. vol. 96; pp. 7131-7136; Jun. 1999.

Chen, et al.; "De Novo Sequencing of Tryptic Peptides Sulfonated by 4-Sulfophenyl Isothiocyanate for Unambiguous Protein Identification Using Post-Source Decay Matrix-Assisted Laser Desorption/Ionization Mass Spectrometry"; Rapid Commun Mass Spectrom 2004; 18: 191-198.

Keough, et al.; "Derivatization Procedures to Facilitate De Novo Sequencing of Lysine-Terminated Tryptic Peptides Using Postsource Decay Matrix-Assisted Laser Desorption/Ionization Mass Spectrometry"; Rapid Commun Mass Spetrom; 14, 2348-2356 (2000).

Lee, et al.; "Highly Informative Proteome Analysis by Combining Improved N-Terminal Sulfonation for De Novo Peptide Sequencing and Online Capillary Reverse-Phase Liquid Chromatography/Tandem Mass Spectrometry"; Proteomics 2004, 4, 1684-1694.

Alley, et al.; "Improved Collision-Induced Dissociation Analysis of Peptides by Matrix-Assisted Laser Desorption/Ionization Tandem Time-of-Flight Mass Spectrometry Through 3-Sulfobenzoic Acid Succinimidyl Ester Labeling"; Journal of Proteome Research 2007, 6, 124-132.

Johnson, et al.; "Novel fragmentation process of peptides by collision-induced decomposition in a tandem mass spectrometer: differentiation of leucine and isoleucine" Anal. Chem., 1987, 59 (21), pp. 2621-2625.

Beardsley, et al.; "Optimization of Guanidination Procedures for MALDI Mass Mapping"; Anal. Chem. 2002, 74, 1884-1890.

Conrotto, et al.; "Peptide De Novo Sequencing with MALDI TOF/TOF: A Simple Approach Using Sulfonation Chemistry"; Sep. 2006; American Biotechnology Laboratory; pp. 12-14.

Gevaert; et al.; "Protein Identification Methods in Proteomics"; Electrophoresis 2000, 21, 1145-1154.

Conrotto, et al.; "Sulfonation Chemistry as a Powerful Tool for MALDI TOF/TOF De Novo Sequencing and Post-Translational Modification Analysis"; Journal of Biomolecular Techniques, vol. 16, Issue 4, Dec. 2005; pp. 441-452.

Steen, et al.; "The ABC's (and XYZ's) of Peptide Sequencing"; Nature Reviews Molecular Cell Biology; vol. 5; Sep. 2004; pp. 699-711.

* cited by examiner

MASS SPECTROMETRY-BASED PROTEIN IDENTIFICATION METHOD WITH SELECTIVE N-TERMINUS DERIVATIZATION

CROSS-REFERENCE TO RELATED APPLICATIONS

The present application is a continuation of pending International Patent Application PCT/HR2011/000002 filed on Jan. 11, 2011 which designates the United States and claims priority from Croatian Patent Application No. P20100044A filed on Jan. 25, 2010, the content of which is incorporated herein by reference.

FIELD OF THE INVENTION

The present invention relates to methods of detection and identification of amino acid sequences, proteins and peptides.

BACKGROUND OF THE INVENTION

Protein identification by peptide mass fingerprinting (PMF) using the MS/MS techniques (tandem mass spectrometry) post-source decay (PSD) or collision-induced dissociation (CID) is based on the comparison of experimentally derived data with theoretically calculated masses in databases (Gevaert et al. Electrophoresis 2001). However, since the genome sequence of most organisms is still incomplete, information on particular proteins is not included in existing databases. In addition, even if relevant protein information existed in the databases, different modifications such as post-translational modifications can hamper identification of a portion or a complete amino acid sequence. Therefore, complete determination of primary protein structure requires detection of an amino acid sequence with the minimal use of databases, i.e., de novo peptide and protein sequencing (H. Steen et al. Mol. Cell. Biol. 2004). The latter is based on tandem mass spectrometry, MS/MS or PSD experiments. In order to facilitate interpretation of complex spectra, peptides are chemically derivatized by appropriate reagents that either almost exclusively or in most of the cases give rise to one series of fragment ions. Mass difference between consecutive signals reveals amino acid sequence. Keough's idea of binding acidic group with N-terminus of peptide has proved successful. Such derivatized peptide bearing positive and negative charge at the same time can be depicted by the following formula: $^-O_3S$—$C_6H_5$-$A_1$-$A_2$-$A_3$-$A_4$-$A_5$-$X^+$, where A stands for any amino acid, and X for lysine or arginine (T. Keough et al. Proc. Natl. Acad. Sci. 1999, T. Keough et al. Rapid Commun. Mass Spectrom. 2000).

If derivatization by acidic group at N-terminus is performed on lysine peptide, then $\epsilon$-amino group of lysine is chemically modified with imidazole group (so called Lys-tag) as to increase the portion of these ions in gas phase and at the same time to enable selective reaction of acidic group with N-terminus (R. L. Beardsley et al. Anal. Chem. 2002). This procedure is known as guanidination. Since the most basic peptide group is already protonated (arginine or guanidinated lysine), an additional proton needed for molecule ionization randomly selects the site of protonation. Peptide bond breaks at the site of protonation resulting in the formation of b- and y-ion series products. However, fragments comprising $SO_3^-$ will not be detected during the MS/MS scan of positive ions due to their instability, so that mass spectrum reveals only y-ion series signals without mass increments, as if derivatization of N-terminus has not been performed (P. Conrotto et al. J. Biomol. Techn. 2005, P. Conrotto et al. Am. Biotechnol. Lab. 2006).

Current procedures of peptide or protein derivatization yield better results in comparison with complex analysis of non-derivatized peptides. However, obtained spectra have not demonstrated sufficiently intense ion signals necessary for detection of amino acids in the spectrum. Furthermore, high level of background noise additionally contributed to imprecise amino acid detection in the spectrum and consequently to imprecise detection of amino acid sequence, i.e., to imprecise peptide or protein identification.

The most common sulfonyl group-containing reagents used in peptide or protein derivatization are 2-sulfobenzoic acid (T. Keough et al. Proc. Natl. Acad. Sci. 1999), sulfo-NHS esters (N-hydroxysuccinimide, NHS; W. R. Allery et al. J. Prot. Research 2007), and 4-sulfophenyl isothiocyanate (P. Chen et al. Rapid Commun. Mass Spectrom. 2004), which relatively quickly (up to 30 minutes) modify peptide and make it amenable to sequencing. Current literature describes sulpho-derivatization reagents based on the following reactive groups: isothiocyano (Y. H. Lee et al. Proteomics 2004), isocyano (P. Conrotto et al. J. Biomol. Techn. 2005), cyclic anhydride (T. Keough et al. Proc. Natl. Acad. Sci. 1999), and N-Hydroxysuccinimide (W. R. Allery et al. J. Prot Research 2007).

In the state of the art there are several patents/patent applications that reveal different methods of detection of amino acid sequence and/or identification of proteins, peptides. However, none of the below stated documents reveal derivatization of peptides or proteins in such a way as to produce negative ions that might be detected in negative MS/MS spectrum.

WO2000043792 describes a procedure based on the use of the compounds with one or more acidic groups with pKa lower than 2 for derivatization of peptide N-terminus. Furthermore, this invention implies that derivatized y-ions are used for analysis of fragments by mass spectrometry, which are devoid of a- and b-ions. Although derivatives of disulfonic acids are also mentioned as acidic groups, derivatization procedure described in this document is not used for spectra analysis in negative MS/MS mode.

WO2002008767 refers to derivatization of lysine-containing peptides. As in the document mentioned above, derivatization procedure in this document is not used for spectra analysis in negative MS/MS mode. Furthermore, this document refers to guanidination, i.e., imidolization of lysine, which is not necessary with the use of the subject invention.

WO2002095412 describes the use of water-stable reagents for peptide derivatization. The reagents comprise one or more sulfonyl groups bound with activated acidic group via aliphatic or aromatic linkage. Activated acid derivatives described in this patent application are acid esters, anhydrides of organic and inorganic acids. The activated acidic moiety particularly mentioned in this patent is NHS ester, allowing for all procedure steps to be carried out under aqueous conditions. The four basic steps in the subject invention include guanidination of lysine. Furthermore, this invention refers to the y-ions analysis in positive mode of operation of mass spectrometer. Derivatization procedure in this document is not used for spectra analysis in negative MS/MS mode.

WO2002095419 holds priority of the application WO2002095412, and, therefore, shares a high level of similarity with the latter patent. In comparison with aforementioned patent, it has been added that polypeptides are immobilized on the solid support, at least in the step "a". This means that complete derivatization procedure is not carried out in solution, the latter being the case with subject inventions. In addition, derivatization procedure in the aforementioned document is not used to analyse spectra in negative MS/MS mode.

European patent application EP 1561755 describes compounds with disulfide bond that react with peptide N-terminus followed by disulfide bond cleavage under oxidation or reduction conditions resulting in the formation of sulfonic acid derivatives. Functional group of disulfide compound that reacts with N-terminus was chosen among carboxyl group, isothiocyanate, succinimidyl oxycarbonyl groups, p-nitrophenoloxy carbonyl groups, pentafluorophenyloxy carbonyl groups, and tetrafluorosulpho phenyloxycarbonyl groups. Subject invention is used for detection of amino acid sequence by y-ions analysis in positive mode of operation of mass spectrometer. In this invention, guanidination of lysine is also necessary. In addition, derivatization procedure in the aforementioned document is not used for spectra analysis in negative MS/MS mode.

WO2005078451 improves previous methods in such a way that removal of unmodified portions of peptides from the solution by ion exchange precedes the analysis of fragments in positive mode of operation of mass spectrometer. This procedure is used after any chemically-aided peptide derivatization.

Accordingly, the conventional procedure of peptide derivatization in the state of the art was carried out by introduction of sulfonyl groups to the N-terminus. N-terminus derivatized in this manner becomes negatively charged. Positively charged C-terminus is a counterbalance to negatively charged N-terminus resulting in the formation of the so called zwitterion, i.e., charge of derivatized protein or peptide equals zero. In further ionization procedure in mass spectrometer used in the state of the art, proton was added to peptide/protein reducing the energy necessary for peptide bonds cleavage, which produced mostly b- and y-ions. Since b-ions would be neutral due to negative charge at N-terminus, only positive y-ions in positive mode of operation of mass spectrometer were analysed in the state of the art.

SUMMARY OF THE INVENTION

Based on the knowledge comprised in the state of the art that refers to methods of detection of amino acid sequence and/or identification of peptides, proteins, a novel procedure for peptide/protein derivatization has been developed using compounds comprising two or more sulfonyl groups, which bind with N-terminus of proteins or peptides. A special embodiment of the subject invention enables selective linking of the compound with two sulfonyl groups to the N-terminus of proteins or peptides without requirement for previous guanidination or protection of lysine by protective groups in peptide/protein. The final reaction product shows improved ability to cleave peptides/proteins in the mass spectrometer in comparison with the product obtained by a derivatization reaction with a compound having one sulfonyl group. Accordingly, the present invention ensures more accurate and precise analysis and detection of amino acid sequence of peptides/proteins, i.e., identification of peptides/proteins in comparison with methods in the state of the art, and analysis of amino acid sequence in a way that has never been described/invented before.

The method of detection of amino acid sequence of peptides/proteins, i.e., method of identification of peptide/proteins in accordance with the invention comprises the following steps:

derivatization of peptides and/or proteins at their N-terminus by a derivatization compound comprising two or more sulfonyl groups, and a reactive group that binds with the amino group of the N-terminus;

analysis of one or more derivatized analytes by acquisition of spectra of derivatized negative ions in a negative mode of operation of a mass spectrometer;

interpretation of obtained fragmentation pattern data to detect amino acid sequence, i.e., to identify aforementioned analyte.

The step of derivatization of peptides and/or proteins gives rise to fragmented ions. More precisely, this step produces positive ions and derivatized negative ions. During derivatization in the subject invention with the compound comprising two sulfonyl groups, one sulfonyl group neutralizes the positive ion charge, whereas the other sulfonyl group gives a negative charge to derivatized ion. This new and unexpected effect allows detection of obtained derivatized negative ions in negative mode of operation of a mass spectrometer. None of the currently known derivatization methods enabled acquiring of MS/MS spectrum of negative ions after derivatization by the compounds having one sulfonyl group, because such method would produce a zwitterion (an ion bearing positive and negative charge) that would remain undetected (P. Conrotto et al. Am. Biotechnol. Lab. 2006). The advantage of the present method is that the signal detected in a MS/MS scan of derivatized negative ions predominates over the signals of positive y ions obtained by derivatization by the compounds comprising one, two or more sulfonyl groups for 5-fold in an absolute amount measured for an equal amount of analyte applied onto MALDI plate.

The term "derivatization compound" in the subject invention refers to any chemical compound that comprises two or more sulfonyl groups and reactive group that binds to amino group.

The term "reactive group" in the subject invention refers to any functional group known to the person skilled in the relevant art to react with amino group.

The term "analyte" in the subject invention refers to any portion (segment) of peptide and/or protein produced in the derivatization step, analysed in mass spectrometer.

DETAILED DESCRIPTION OF THE INVENTION

The method presented by the subject invention enables detection of complete amino acid sequence of proteins, i.e., peptides. In protein identification, protein cleavage with known chemical or enzymatic proteolytic procedures precedes the method of the subject invention. Thus, proteins can be cleaved for example with chemical compounds such as ninhydrin, cyanogen bromide or by simple degradation using acid hydrolysis. Furthermore, proteins can be cleaved with enzymes such as trypsin, chymotrypsin, thermolysin, Lys-C, Glu-C, Arg-C, etc.

Figure 1:
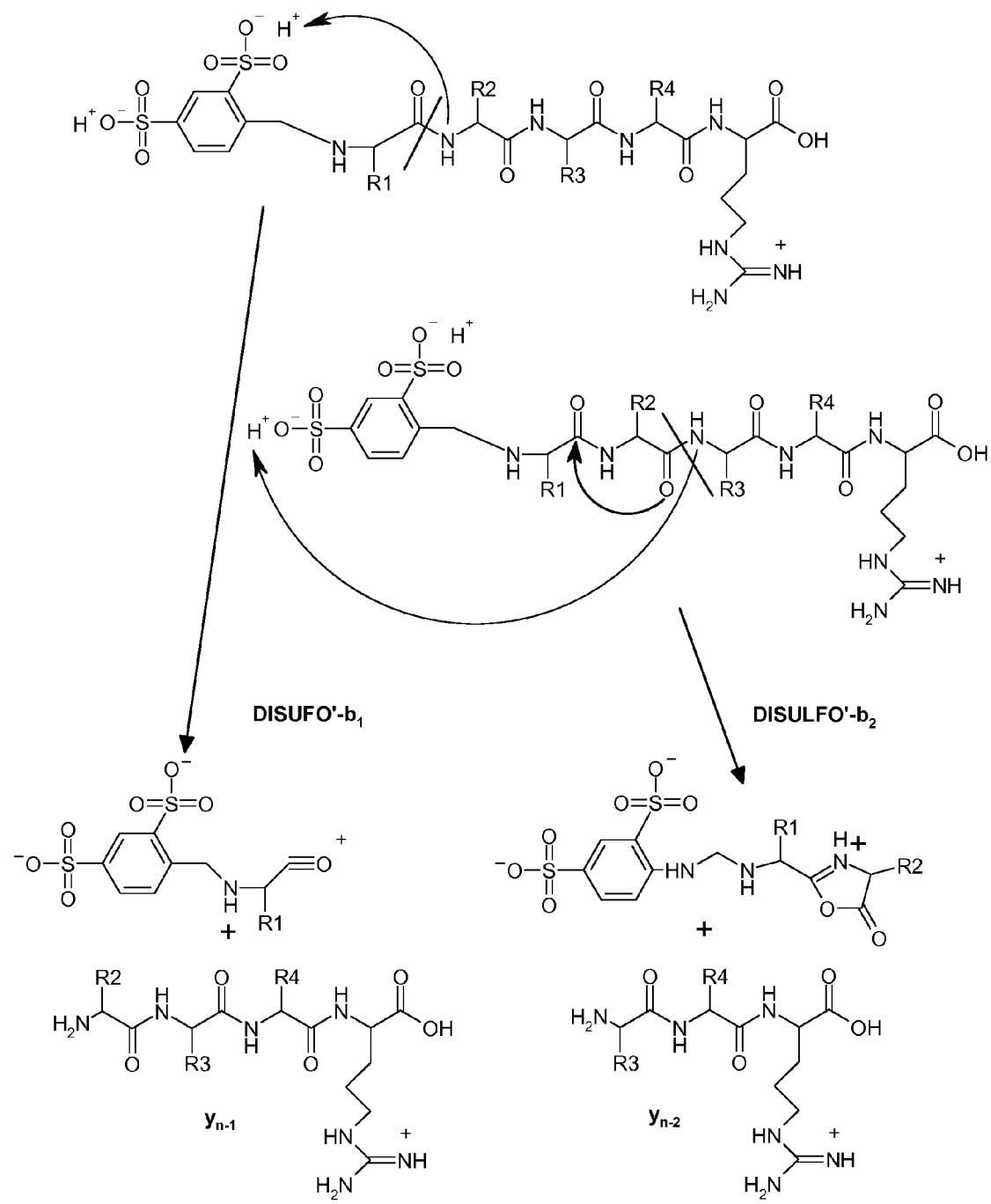
FIG. 1 represents cleavage mechanism of analytes in mass spectrometer.

The procedure of protein proteolysis into peptides up to 5000 Da is followed by peptide mass determination by mass spectrometry and thereafter by the peptide derivatization procedure. A derivatization compound comprising two sulfonyl groups is added to aqueous solution of peptides/proteins to be derivatized. Chemical compounds used in the derivatization step in the subject invention comprise two sulfonyl groups and reactive group which binds to amino group. The derivatization compound binds to N-terminus of peptide via reactive group giving it two sulfonyl groups and increasing its mass. Therefore, during the mass spectrometry, it is necessary to add the m/z value of the relevant derivatization compound comprising two sulfonyl groups to the peptide mass (in the positive mode of operation the reagent is detached during analyses yielding products that can reveal amino acid sequence, whereas in the negative mode of operation the reagent is not detached from N-terminus, but the formation of products revealing amino acid sequence is still increased). Therefore, the N-terminus is doubly negatively charged, whereas the C-terminus or some basic side branch of peptide and/or protein is positively charged. When sulfonyl groups donate labile protons to amide groups, peptide and/or protein dissociates into amino acid integral portions. The resulting positive ions do not differ in mass from the positive ions of non-derivatized analogue, since sulfonyl groups during proton donation to amide bond in the peptide cleave off either a portion of ions from N-terminus of peptide chain or derivatization compound itself, thus producing gradually shorter peptide/protein ions. The same mechanisms in the negative mode of operation yields the final reaction products, i.e., negatively charged derivatized ions comprising two sulfonyl groups at N-terminus, which increase the mass of precursor ions and product ions for the mass values of derivatization reagent (FIG. 1). However, regardless of the addition of derivatization group, the differences between detected ions in positive or negative mode of operation of mass spectrometry are equal, which ultimately enables determination of amino acid sequence or their modifications.

Derivatized negative ions can be analysed in different mass spectrometers. Thus, the following mass spectrometers are used: time-of-flight (TOF), tandem mass analyzers (MS/MS, QQQ, MS/Q, Q/TOF), quadropole (Q), ion trap (IT) and similar devices. Moreover, experiments have shown that the use of MALDI ion source in the subject invention gives rise to exclusively y fragments of positive ions and derivatized negative b-ions. Signals obtained by analysis of these derivatized negative b-ions produced in the subject procedure are extremely strong, and noise in comparison with standard methods of detection of amino acid sequence or identification of peptide/protein is up to 10-fold lower. Thus, the overall increase of signal intensity obtained by the subject invention is up to 15-fold higher than the signal intensities obtained by the methods in the state of the art. However, by applying ion sources that cleave peptides/proteins in a different manner, it is possible to obtain with the subject invention also other fragments of negative and positive ions, maintaining the basic component of amino acid sequence determination based on the difference between masses of signal sequence.

The reactive group of a derivatization compound can be any group reacting with amino group. It is preferable that the reactive group of the compound used in the derivatization step of the subject invention is selected from the group comprising aldehyde, keto-, isothiocyanate-, isocyanate-group, NHS ester (N-hydroxysuccinimide ester), anhydride or activated carboxylic acid group.

It is most preferred that, in the subject invention, the reactive group of the derivatization compound is an aldehyde group. In the cases where in the subject invention compound with an aldehyde reactive group at ph 1-5 is used, the aldehyde group selectively reacts with N-terminus of peptide or protein, without binding to other amino groups in protein or peptide chain. By using this approach, dual derivatization of tryptic peptides is avoided, since derivatization reaction performed according to the subject invention selectively derivatizes N-terminus without the need of adding protective group at lysine. Since in this case lysine guanidination is redundant, the method of detection of amino acid sequence, i.e., peptide/protein identification is additionally simplified. Also, since guanidination, which causes significant quantitative losses during sample handling, is not needed, signal intensity in the analysis of derivatized negative ions in negative mode of operation of mass spectrometry is increased. It is most preferred that compound with aldehyde group in derivatization step is used at approximately pH 4. Furthermore, it is preferable that during the use of a derivatization compound with aldehyde reactive group, $NaBH_3CN_4$ is also added to aqueous solution as to reduce imino-group of the resulting Schiff base.

Experiments have shown that the presence of aldehyde reactive groups in a derivatization compound enables a selective derivatization reaction at the N-terminus, even in a derivatization reaction with compounds comprising only one sulfonyl group. In fact, also in such cases, it appeared that lysine guanidination prior to derivatization step with one sulfonyl group was unnecessary, and that unprotected lysine would not react with the aforementioned compounds. However, since in this case, only y positive ions could be analyzed, detection procedure of amino acid sequence itself did neither result in particularly intensive signals nor exert low or non-existing noise, as it is the case in derivatization by the compound comprising two sulfonyl groups.

Furthermore, it is most preferred to use 4-formylbenzene-1,3-disulfonic acid as compound in derivatization step.

EXAMPLE 1

Use of 4-formylbenzene-1,3-disulfonic acid as a derivatization compound

In this example the method of peptide derivatization of the subject invention by chemical reaction in two stages was used: first stage includes condensation of aldehyde and primary amine with production of Schiff base, and the second stage includes reduction of imines of Schiff base into amines. The reagents used included: 4-formylbenzene-1,3-disulfonic acid of company Sigma Aldrich (St. Louis, Mo., USA), $NaBH_3CN_4$ (Merck, Darmstadt, Germany), and peptides obtained by trypsin autolysis (Merck, Darmstadt, Germany), CHCA matrix (α-cyano-4-hydroxycinnamic acid, Sigma Aldrich, St. Louis, Wis., USA).

Table 1 presents known trypsin peptides and their ions detected by mass spectrometry, which are produced during trypsin autolysis prior to derivatization by 4-formylbenzene-1,3-disulfonic acid.

TABLE 1

| Peptides produced by trypsin autolysis with theoretical calculation of masses of corresponding ions. | | |
|---|---|---|
| FRAGMENT | m + H | sequence |
| T1 | 262.1510 | SR |
| T2 | 515.6368 | IQVR |

TABLE 1-continued

Peptides produced by trypsin autolysis with theoretical calculation of masses of corresponding ions.

| FRAGMENT | m + H | sequence |
|---|---|---|
| T6 | 842.5094 | VATVSLPR |
| T5 | 1045.5636 | LSSPATLNSR |
| T7 | 1768.7993 | SCAAAGTECLISGWGNTK |
| T3 | 2211.1000 | LGEHNIDVLEGNEQFINAAK |
| T4 | 2283.1800 | IITHPNFNGNTLDNDIMLIK |
| T5 | 906.5043 | NKPGVYTK |
| T2 | 1006.4874 | APVLSDSSCK |
| T1 | 1469.7305 | SSGSSYPSLLQCLK |
| T6 | 1736.8425 | VCNYVNWIQQTIAAN |
| T3 | 2158.0307 | SSYPGQITGNMICVGFLEGGK |
| T4 | 3013.3227 | DSCQGDSGGPVVCNGQLQGIVSWGYGCAQK |

Upon purification of 1 μg fragments derived from trypsin autolysis using ZipTip technique, a peptide mixture was evaporated using SpeedVac (Eppendorf, Germany) concentrator followed by addition of 1 mg 4-formylbenzene-1,3-disulfonic acid and 4 mg NaBH$_3$CN$_4$ dissolved in 100 μl phosphate buffer pH 4.0 to dried concentrate. The solution was stored in the fridge at temperature of 4-8° C. for 12 hours to react. Subsequently, 10 μl of the solution was purified again using ZipTip, dried in SpeedVac concentrator and dissolved in 5 μl CHCA matrix with 5 mg/ml concentration. 1 μl of this solution was applied onto MALDI metal plate and analyzed by mass spectrometer.

The derivatization procedure of peptides obtained by protein cleavage by trypsin at N-terminus is illustrated by the following reaction:

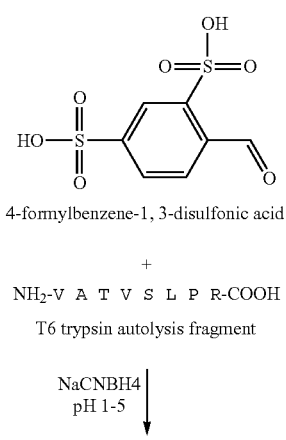

4-formylbenzene-1,3-disulfonic acid

+

NH$_2$-V A T V S L P R-COOH

T6 trypsin autolysis fragment

NaCNBH4
pH 1-5

-continued

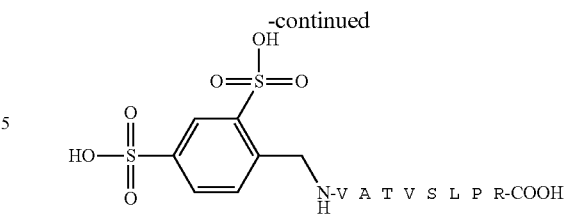

N-V A T V S L P R-COOH
H

The example of instrumental MS/MS fragmentation of analytes originally derived from trypsin autolysis shows significant improvement of structural analysis of produced analytes, which increases accuracy of amino acid sequence detection (so called de novo sequencing of unknown peptides).

Figure 2A:
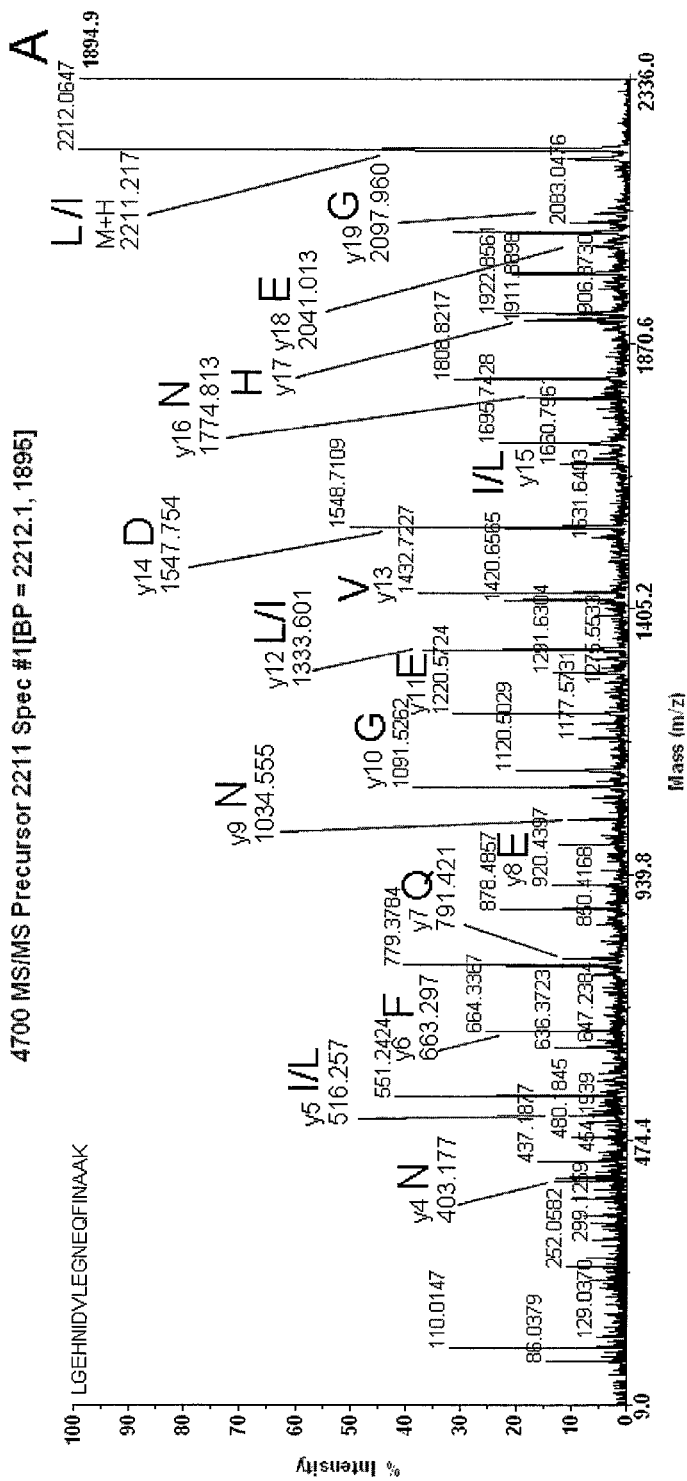
FIG. 2 represents MS/MS mass spectra of: (2A) non-derivatized analyte, (2B) peptide derivatized with derivatization compound with two sulfonyl groups acquired in the positive mode of operation of mass spectrometer, and (2C) peptide derivatized with derivatization compound with two sulfonyl groups acquired in negative mode of operation of mass spectrometer.
Figure 2B:
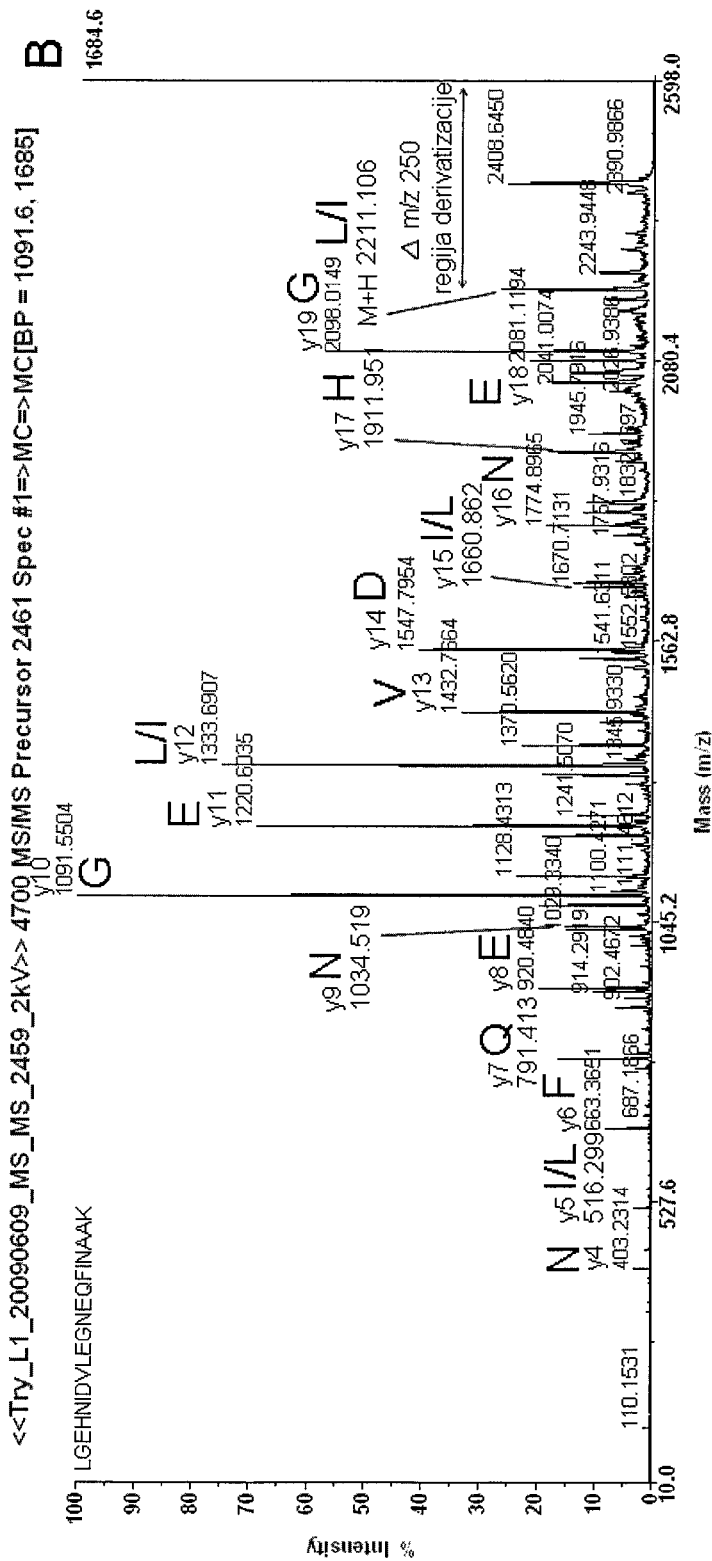
Figure 2C:
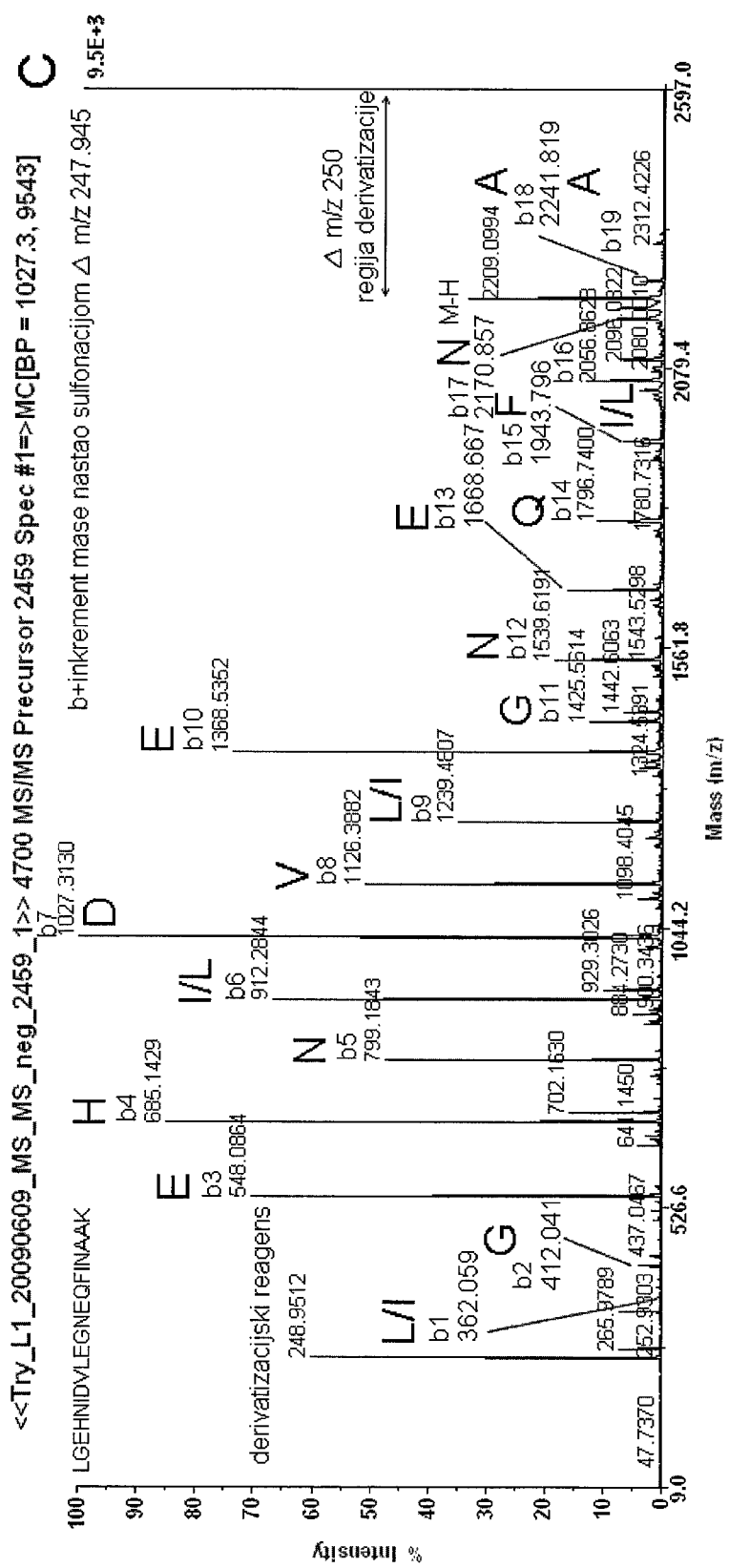

For the purpose of evaluation of the success of the method, MS/MS spectra were acquired on MALDI-TOF/TOF instrument before and after derivatization. An example presented in FIG. 2 gives a comparison of MS/MS spectra of positive ions of underivatized lysine fragment LGEHNIDVLEGNEQFI-NAAK (FIG. 2A) and MS/MS spectra of positive (FIG. 2B) and negative ions (FIG. 2C) of the same derivatized fragment. It is important to point out that MS/MS spectra of both positive and negative derivatized ions are acquired on the same sample, i.e., on the same ions obtained after derivatization, only the polarity of electrodes in the instrument is changed. In the example described herein positive y ions and derivatized negative b ions were produced.

Production of positively charged MS/MS ions in mass spectrometer $Y_{n-1}$ i$Y_{n-2}$ ... $Y_{n-190}$ f peptide LGEHNIDVLEG-NEQFINAAK arising from the cleavage of underivatized peptide is shown in FIG. 2A, whereas peptide derivatized with 4-formylbenzene-1,3-disulfonic acid by proton transfer from sulfonic acid groups (added at N-terminus by derivatization) to amide groups on peptide is shown in FIG. 2B). Produced positive y ions do not differ in mass regardless of derivatization, because sulfonyl groups during proton donation to amide bond in peptide cleave off a portion of ions on the corresponding peptide chain, thus producing gradually shorter peptide ions. During MS/MS analysis of negatively charged ions of derivatized fragment, it is possible to detect only b ions that kept sulfonyl groups, which requires that an increment of m/z 247,945 is added (FIG. 2C).

Comparison of three MS/MS mass spectra (FIGS. 2A, 2B and 2C) of equal sample amounts of tryptic fragment LGE-HNIDVLEGNEQFINAAK before (2A) and after derivatization (2B and 2C) reveals partial amino acid sequences of peptide after detection of y ions in the case 2A and 2B LGE-HNIDVLEGNEQFIN, and a complete amino acid sequence after detection of derivatized negative b ions in the case 2C. The last unmarked fragment in MS/MS spectrum in FIG. 2C (lysine, K) was determined by calculation based on subtraction (m/z 2459) from the mass of the finally detected b derivatized fragment (m/z 2312), which yields a difference of m/z 147 that unambiguously belongs to lysine. MS/MS mass spectrum 2A does not have consistent examination of fragments corresponding to MS/MS mass spectrum 2B according to signal intensity, because it is impossible to carry out MS/MS analysis of negative ions (data not shown). Furthermore, in MS/MS mass spectrum in FIG. 2A, detection of y ions was extremely hampered, as noise was increased for one order of magnitude in comparison with MS/MS spectrum in FIG. 2B, and resulting ions can be attributed to a, b, c or x, y, z ions (Novel fragmentation process of peptides by collision-induced decomposition in a tandem mass spectrometer: differentiation of leucine and isoleucine, First PageHi-Res PDF

[568 KB] Richard S. Johnson, Stephen A. Martin, Klaus Biemann, John T. Stults, J. Throck Watson Anal. Chem., 1987, 59 (21), pages 2621-2625) that overlap (e.g. b ion m/z 664,337 overlaps with y ion 663,297; FIG. 2A). In the mass spectrum in FIG. 2B, every y ion has an accompanying y-$NH_3$ ion, which allows for unambiguous detection of y ions (y-$NH_3$ ions can be easily detected from the spectrum at m/z decreased by 17). Such detection of y ions is not possible in mass spectrum in FIG. 2A, since most y ions do not have their accompanying y-$NH_3$ ion. Similarly, decrease in masses of b derivatized ions is observed in MS/MS mass spectrum, but b-$H_2O$ ions are detected (m/z decreased by 18). Comparison of spectra in FIGS. 2A, 2B and 2C shows significant increase in measured ion signals in spectrum in FIG. 2C in comparison with mass spectra in FIGS. 2A and 2C, which proves that the subject method increases success in detection of amino acid sequence of peptide.

As already mentioned, signals detected during detection of negative MS/MS derivatized b ions outmatches the signals of y ions 5-fold in absolute value (9500 in mass spectrum in FIG. 2C versus 1685 in mass spectrum in FIG. 2B) for equal peptide amount applied onto MALDI plate. If up to 10-fold lower noise detected in analysis of derivatized ions is added, the overall increase in signal-to-noise ratio (S/N) after derivatization is 15-fold for MS/MS negative ions. Similar experiments were carried out on all ions presented in Table 1 before and after derivatization, and obtained results do not differ from the results set out in this example.

The method described in the present patent application is technically rapid, cost effective and reliable, and could be of inestimable worth in proteomics analyses of various samples, especially the biological ones. In fact, only in humans the size of the whole proteome is estimated to several million protein species, and databases currently provide information on completely determined amino acid sequences for approximately 500 000 proteins. The described method could, thus, facilitate simple determination of amino acid sequences of unidentified human proteins with significant medical implications (e.g. biomarker discovery). It would also be as simple to identify proteins for different biological species for which publicly accessible protein databases, such as Trembl and SwissProt, contain no exact information on amino acid sequences.

The present method reduces the time of sub-structural analysis of tryptic digests by mass spectrometry (MS/MS analysis), and increases accuracy when searching protein databases.

What is claimed is:

1. A method of detection of an amino acid sequence for identification of peptides and/or proteins, the method comprising the following steps:
   selective derivatization of an N-terminus of a peptide or an N-terminus of a protein having an unprotected ε-amine of lysine versus derivatization of the unprotected ε-amine of lysine, wherein the selective derivatization is carried out at pH 1-5 with addition of sodium cyanoborohydride (NaBH$_3$CN) using a derivatization compound, the derivatization compound comprising an aldehyde group as a reactive group and two or more sulfonic acid groups, wherein the selective derivatization comprises reacting of the aldehyde group with an amino group at the N-terminus of the peptide and/or at the N-terminus of the protein to form derivatized analytes in a form of a secondary amine;
   mass spectrometer analysis of the derivatized analytes by acquiring spectra of derivatized negative ions in a negative mode of operation of a mass spectrometer;
   determining an amino acid sequence of the derivatized analytes by interpretation of fragmentation sequence data obtained from the mass spectrometer analysis.

2. The method of claim 1, wherein the derivatization compound is 4-formylbenzene-1,3-disulfonic acid.

3. The method of claim 1 wherein a spectrum of derivatized b-negative ions is acquired in the negative mode of operation of the mass spectrometer in the analysis of the derivatized analyte.

4. A method of detection of an amino acid sequence for identification of peptides or proteins, the method comprising the following steps:
   selective derivatization of an N-terminus of a peptide or an N-terminus of a protein having an unprotected lysine ε-amine group versus derivatization of the unprotected lysine ε-amine group, wherein the selective derivatization is carried out at pH 1-5 with addition of sodium cyanoborohydride (NaBH$_3$CN) using a derivatization compound, the derivatization compound comprising an aldehyde group as a reactive group and two or more sulfonic acid groups, wherein the selective derivatization comprises reacting the aldehyde group with an amino group at the N-terminus of the peptide or at the N-terminus of the protein to form a derivatized analyte in a form of a secondary amine, wherein the derivatization includes a reduction of a Schiff base imine into an amine;
   mass spectrometer analysis of the derivatized analyte by acquiring spectra of derivatized negative ions in a negative mode of operation of a mass spectrometer;
   determining an amino acid sequence of the derivatized analyte by interpretation of fragmentation sequence data obtained from the mass spectrometer analysis.

5. A method of detection of an amino acid sequence for identification of peptides and/or proteins, the method comprising the following steps:
   selective derivatization of an N-terminus of a peptide or an N-terminus of a protein having an unprotected ε-amine of lysine versus derivatization of the unprotected ε-amine of lysine, wherein the selective derivatization is carried out at pH 1-5 with addition of sodium cyanoborohydride (NaBH$_3$CN) using 4-formylbenzene-1,3-disulfonic acid as a derivatization compound to react with an amino group at the N-terminus of the peptide and/or at the N-terminus of the protein to form derivatized analytes in a form of a secondary amine;
   mass spectrometer analysis of the derivatized analytes by acquiring spectra of derivatized negative ions in a negative mode of operation of a mass spectrometer;
   determining an amino acid sequence of the derivatized analytes by interpretation of fragmentation sequence data obtained from the mass spectrometer analysis.

6. The method of claim 5 wherein a spectrum of derivatized b-negative ions is acquired in the negative mode of operation of the mass spectrometer in the analysis step of the derivatized analyte.

* * * * *